(12) United States Patent
Wiegel

(10) Patent No.: US 12,257,404 B2
(45) Date of Patent: Mar. 25, 2025

(54) FIXING DEVICE FOR FIXING A CATHETER ASSEMBLY TO A PATIENT

(71) Applicant: B. Braun Melsungen AG, Melsungen (DE)

(72) Inventor: Heinz Wiegel, Alheim (DE)

(73) Assignee: Braun Melsungen AG, Melsungen (DE)

( * ) Notice: Subject to any disclaimer, the term of this patent is extended or adjusted under 35 U.S.C. 154(b) by 323 days.

(21) Appl. No.: 17/278,894

(22) PCT Filed: Aug. 13, 2019

(86) PCT No.: PCT/EP2019/071686
§ 371 (c)(1),
(2) Date: Mar. 23, 2021

(87) PCT Pub. No.: WO2020/078601
PCT Pub. Date: Apr. 23, 2020

(65) Prior Publication Data
US 2022/0040455 A1    Feb. 10, 2022

(30) Foreign Application Priority Data
Oct. 17, 2018   (DE) ...................... 10 2018 217 784.8

(51) Int. Cl.
*A61M 25/02*    (2006.01)

(52) U.S. Cl.
CPC ....... *A61M 25/02* (2013.01); *A61M 2025/024* (2013.01); *A61M 2025/028* (2013.01)

(58) Field of Classification Search
CPC ............ A61M 25/02; A61M 2025/024; A61M 2025/028; A61M 16/0497;
(Continued)

(56) References Cited

U.S. PATENT DOCUMENTS 5,069,206 A * 12/1991 Crosbie ............. A61M 16/0493
128/207.14
9,056,186 B2   6/2015 Wright et al.
(Continued)

FOREIGN PATENT DOCUMENTS

DE       102015213686 A1    1/2017

OTHER PUBLICATIONS

German Search Report received in Application No. 10 2018 217 748.8 dated Aug. 14, 2019, 27 pages.
(Continued)

*Primary Examiner* — Joel M Attey
*Assistant Examiner* — Alexandra Lalonde
(74) *Attorney, Agent, or Firm* — Christopher A. Rothe; CM Law

(57) ABSTRACT

A device for fixing a catheter assembly to a patient is disclosed. The device has a receiving unit for connection to a skin surface of the patient. A receiving recess is arranged on the receiving unit to receive a portion of the catheter assembly. A closure unit is movable relative to the receiving recess between an opened state, in which the receiving recess is open for receipt and/or removal of the portion of the catheter assembly, and a closed state, in which the receiving recess is at least partially closed by the closure unit. The closure unit is joined non-releasably to the receiving unit. The receiving unit, at least in part, has shape elasticity such that the closure unit is movable between the opened state and the closed state by elastic deformation of the receiving unit. The device can be used in infusion therapy.

18 Claims, 3 Drawing Sheets

Figure 1:
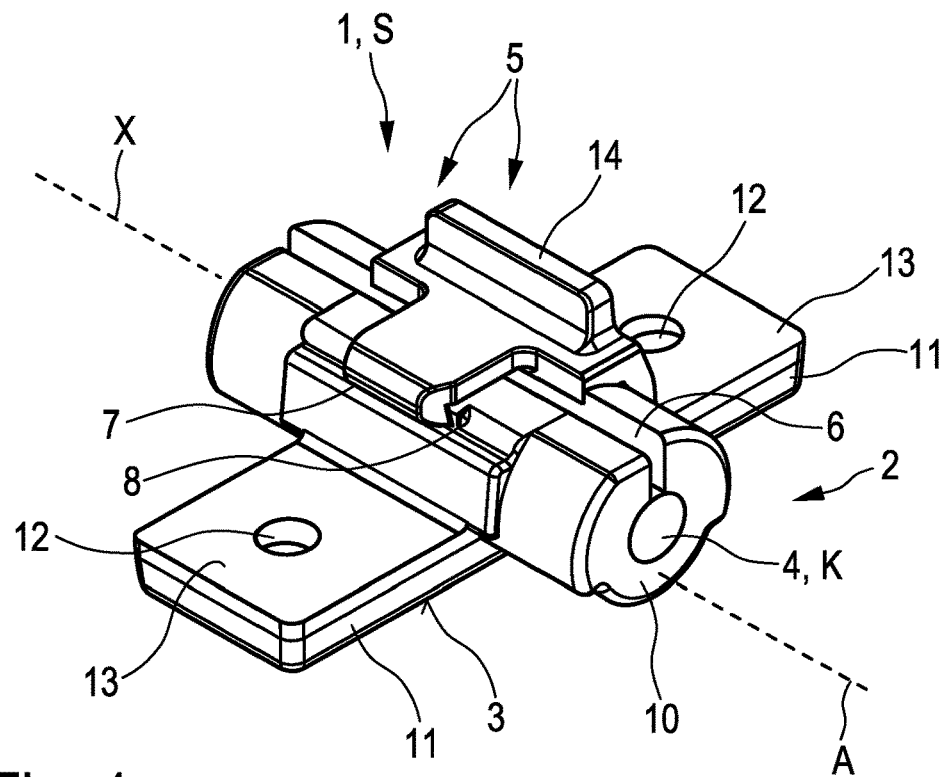

(58) Field of Classification Search
CPC .. A61M 2025/0226; A61M 2025/0246; A61M 2025/0293; A61M 2025/0213; A61M 2025/0206; A61M 2025/0253; A61M 2025/0266; A61M 2205/0216; A61M 2209/088; A61M 2210/04; A61B 17/0487; A61B 17/122; A61B 2017/2808; A61B 50/20; Y10S 128/26
See application file for complete search history.

(56) References Cited

U.S. PATENT DOCUMENTS

| | | | |
|---|---|---|---|
| 2003/0229313 A1* | 12/2003 | Bierman | A61M 25/02 604/174 |
| 2005/0038453 A1* | 2/2005 | Raulerson | A61M 25/02 606/151 |
| 2006/0089600 A1 | 4/2006 | Bierman et al. | |
| 2008/0125718 A1* | 5/2008 | Tsuchiya | A61M 25/02 604/174 |
| 2014/0324024 A1 | 10/2014 | Tejani | |
| 2014/0343501 A1 | 11/2014 | Bierman et al. | |
| 2017/0072168 A1* | 3/2017 | Karim | A61M 25/02 |
| 2018/0339136 A1* | 11/2018 | Wood | A61M 25/02 |

OTHER PUBLICATIONS

International Search Report received in Application No. PCT/EP2019/071686 dated Nov. 19, 2019, 13 pages.
Written Opinion received in Application No. PCT/EP2019/071688 dated Nov. 19, 2019, 17 pages.
Search Report received in German Application No. 10 2018 217 784.8 dated Aug. 14, 2019, with translation, 20 pages.
Written Opinion received in Application No. PCT/EP2019/071688 dated Nov. 19, 2019, with translation, 14 pages.
Office Action received in Chinese Application No. 201980068491.4 dated Aug. 22, 2022, with translation, 8 pages.

* cited by examiner

FIXING DEVICE FOR FIXING A CATHETER ASSEMBLY TO A PATIENT

CROSS-REFERENCE TO RELATED APPLICATION(S)

This application is the United States national stage entry of International Application No. PCT/EP2019/071686, filed Aug. 13, 2019, and claims the benefit of priority of German Application No. 10 2018 217 784.8, filed Oct. 17, 2018. The contents of International Application No. PCT/EP2019/071686 and German Application No. 10 2018 217 784.8 are incorporated by reference herein in their entireties.

FIELD

The invention relates to a fixing device for fixing a catheter assembly to a patient, having a receiving unit, which is provided for connection to a skin surface of the patient, a receiving recess, which is arranged on the receiving unit and is provided to receive a portion of the catheter assembly, and a closure unit, which is movable relative to the receiving recess between an opened state, in which the receiving recess is open for receipt and/or removal of the portion of the catheter assembly, and a closed state, in which the receiving recess is at least partially closed by means of the closure unit.

BACKGROUND

A fixing device of this kind is known from U.S. 9,056,186 B2 and has a receiving unit in the form of a main body. The main body is provided for connection to a skin surface of the patient and has a receiving recess. The receiving recess is provided to receive a V-shaped branching portion of the catheter assembly. In the known fixing device, the receiving recess is configured in such a way that the branching portion is secured axially on the receiving recess with form-fit engagement. Moreover, a closure unit in the form of a cover is provided, which is movable relative to the receiving recess. The cover is movable between an opened state and a closed state. In the closed state, the cover is latched onto the main body and closes the receiving recess at the top, such that the branching portion is also secured in the receiving recess perpendicularly with respect to the axial direction. In the opened state, the receiving recess is partially open, such that the branching portion can be introduced into the receiving recess or can be removed therefrom. In the known fixing device, the cover is designed as a structural part produced separately from the main body, and it is separated from the main body in the opened state.

SUMMARY

The object of the invention is to make available a fixing device of the type mentioned at the outset, which fixing device permits simple and safe handling and at the same time permits a particularly simple structure.

This object is achieved by the fact that the closure unit is joined non-releasably to the receiving unit, wherein the receiving unit is designed at least in part with shape elasticity, such that the closure unit is movable between the opened state and the closed state by means of an elastic deformation of the receiving unit. The solution according to the invention on the one hand prevents loss of the closure unit in the opened state. This is because the closure unit is joined non-releasably to the receiving unit. This permits safe handling and also a particularly simple structure of the fixing device. On the other hand, the solution according to the invention at the same time permits a particularly simple movement of the closure unit between the opened state and the closed state. This also contributes to particularly simple and safe handling of the fixing device. For this purpose, the receiving unit is designed at least in part with shape elasticity, such that the closure unit is movable by means of an elastic deformation of the receiving unit. This likewise contributes to a particularly simple structure of the fixing device. Within the meaning of the invention, joined non-releasably means that the closure unit and the receiving unit cannot be separated without being destroyed. The receiving unit and the closure unit can be joined non-releasably in particular by force-fit engagement, form-fit engagement and/or cohesive bonding. There is preferably a cohesively bonded connection. Moreover, it is particularly advantageous if the closure unit and the receiving unit are formed as one continuous piece. The receiving unit can be given shape elasticity by means of a suitable choice of material and/or by means of a design feature. For example, the receiving unit can at least in part be designed with a thin wall and/or made of a material that has shape elasticity. The receiving unit can in particular be designed to be elastically extensible, shearable and/or bendable. The receiving unit is preferably designed to be bendable with shape elasticity, such that the closure unit is pivotable between the opened state and the closed state by means of an elastic bending deformation of the receiving unit. The whole receiving unit is preferably designed with shape elasticity. It is advantageous if the receiving unit has a rear face which is directed away from the receiving recess and which is provided to bear on the skin surface. To connect the receiving unit to the skin surface, it can in a customary manner be adhesively affixed to the skin surface or sutured onto the latter. For the latter connecting option, the receiving unit can have fastening portions which protrude in particular in the manner of wings and which are each provided with a through-bore as a passage for a suture material. The receiving recess can in particular be configured in such a way that a branching portion or a hose portion of the catheter assembly is, in the closed state, secured with force-fit and/or form-fit engagement on and/or in the receiving recess. The receiving recess is preferably channel-shaped and provided to receive a hose portion of the catheter assembly. The channel-shaped receiving recess can engage around the hose portion in the circumferential direction, in such a way that said hose portion is secured frictionally in the axial direction on the receiving recess. In the closed state, the closure unit can at least partially close the receiving recess with form-fit and/or force-fit engagement. For this purpose, the closure unit can be designed in particular in the form of a latch, plug or clamp unit.

The solution according to the invention is suitable in a particularly advantageous manner for fixing a central venous catheter to a patient. However, the solution according to the invention can also be used for fixing other kinds of catheter assemblies to a patient.

In one embodiment of the invention, the receiving unit is made of a flexible plastic and the closure unit is made of a substantially dimensionally stable plastic. By virtue of the flexible design of the receiving unit as a whole, it is possible in particular to compensate for any production-related dimensional deviations of the portion of the catheter assembly that is to be fixed. This is because the receiving recess is likewise elastically resilient on account of the receiving unit being made of flexible plastic. Moreover, the flexible design of the receiving unit counteracts irritation of the skin surface that is lying on the receiving unit. An elastomer or a silicone elastomer can be used in particular as the flexible plastic. By producing the closure unit from a substantially dimensionally stable plastic, a secure closure of the receiving recess in the closed state is ensured in particular.

In a further embodiment of the invention, the receiving unit and the closure are made as one continuous piece in the form of a multi-component injection molding from at least two different plastics. Methods for producing multi-component injection moldings from plastic are well known. The fixing device is preferably produced in the form of a two-component injection molding. This is a particularly advantageous embodiment of the invention. Firstly, the production using two components permits a particularly reliable and cost-effectively producible non-releasable join between the closure unit and the receiving unit. Secondly, the overall production of the fixing device proves cost-effective and straightforward.

In a further embodiment of the invention, the receiving recess is designed in the form of an elongate channel, which has a longitudinal slit for the introduction of a hose portion of the catheter assembly into the channel, wherein a slit width of the longitudinal slit is modifiable by means of the elastic deformation of the receiving unit. The channel serves to receive the hose portion. To introduce the hose portion into the channel and to remove the hose portion from the channel, the longitudinal slit is provided, which preferably extends along the entire length of the channel. The channel, at least in the closed state, preferably has a substantially circular cylindrical basic shape, which is adapted to a shape of the hose portion that is to be fixed. In this embodiment, it is particularly advantageous if the receiving unit has shape elasticity at least in the region of the receiving recess. In this way, it is possible to compensate for tolerance-related deviations in the shape of the hose portion. For still better fixing, the channel can be provided with a profile, in particular a zigzag-shaped or undulating profile.

In a further embodiment of the invention, the closure unit, in the closed state, causes an at least partial elastic prestressing of the channel in the radial direction of the channel, in order to frictionally fix the hose portion in the axial direction of the channel. To put it simply, the channel is radially compressed in the closed state by means of the closure unit. This permits particularly secure fixing of the hose portion.

In a further embodiment of the invention, the closure unit has a latching portion and a complementary mating latching portion, wherein the latching portion and the mating latching portion are movable relative to each other by means of the elastic deformation of the receiving unit. The latching portion and the mating latching portion are held on each other with form-fit engagement in the closed state and are freed from each other in the opened state. The latching portion can be designed in particular in the form of a latching lug, a latching hook or similar. The mating latching portion can be designed in particular in the form of a latching projection, a latching depression or similar. In relation to a longitudinal direction of the receiving recess, the latching portion is preferably secured on one side of the receiving recess, and the mating latching portion is secured on the other side of the receiving recess. For the movement between the opened state and the closed state, the latching portion and the mating latching portion can be movable relative to each other in rotation and/or translation.

In a further embodiment of the invention, the latching portion and the mating latching portion are pivotable relative to each other about a pivot axis, wherein the receiving unit has an elastic flexure portion which permits the relative pivotability of the latching portion and of the mating latching portion. The pivot axis is preferably oriented parallel to a longitudinal direction of the receiving recess. In relation to a vertical direction of the fixing device, the flexure portion is preferably arranged beneath the receiving recess. The flexure portion permits an elastic bending deformation of the receiving unit. The receiving unit is elastic at least in the region of the flexure portion. However, it is possible for the whole receiving unit to have shape elasticity. The flexure portion is preferably formed by means of a geometric weakening, in particular a reduced wall thickness, of the receiving unit. The geometric weakening, in particular the reduced wall thickness, is preferably provided by means of the receiving recess. In this embodiment of the invention, it is particularly advantageous if the receiving recess is designed in the form of an elongate channel.

BRIEF DESCRIPTION OF THE DRAWING FIGURES

Further advantages and features of the invention will become clear from the following description of a preferred exemplary embodiment of the invention, which is shown in the drawings.

Figure 2:
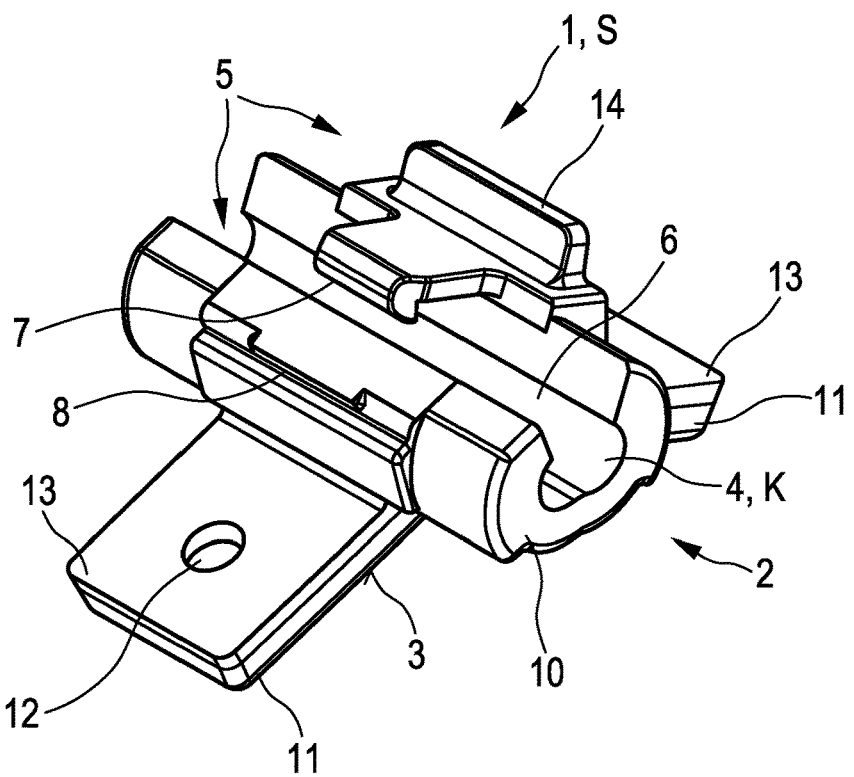
Figure 3:
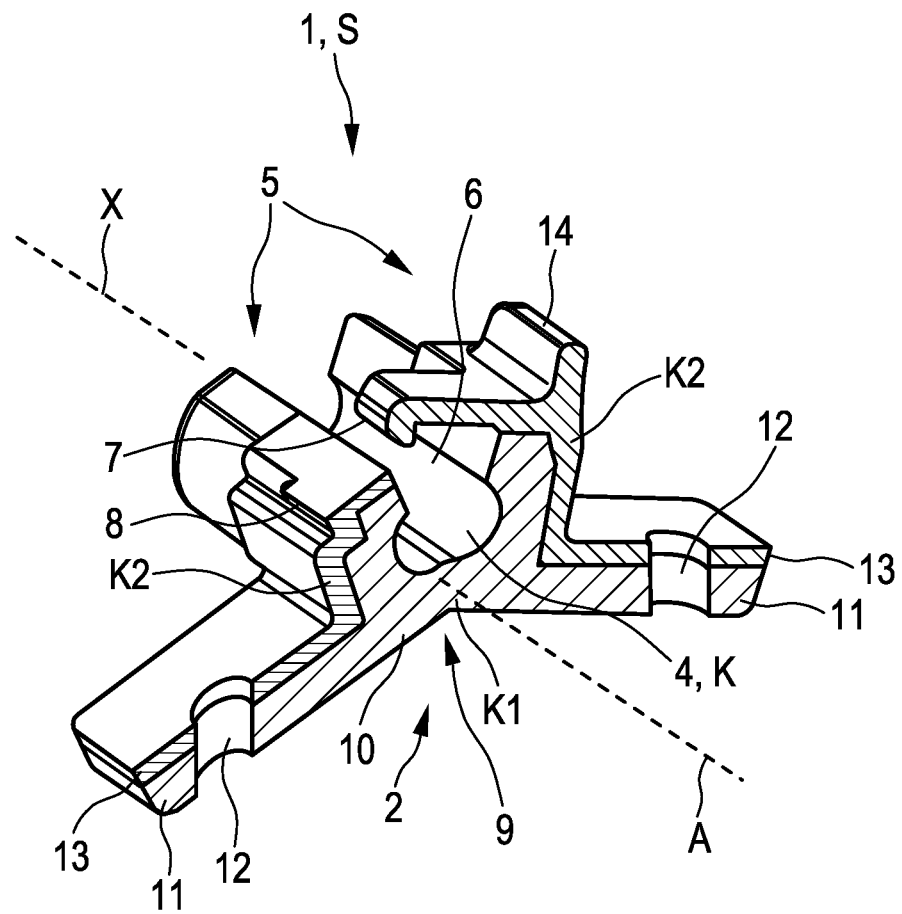
Figure 4:
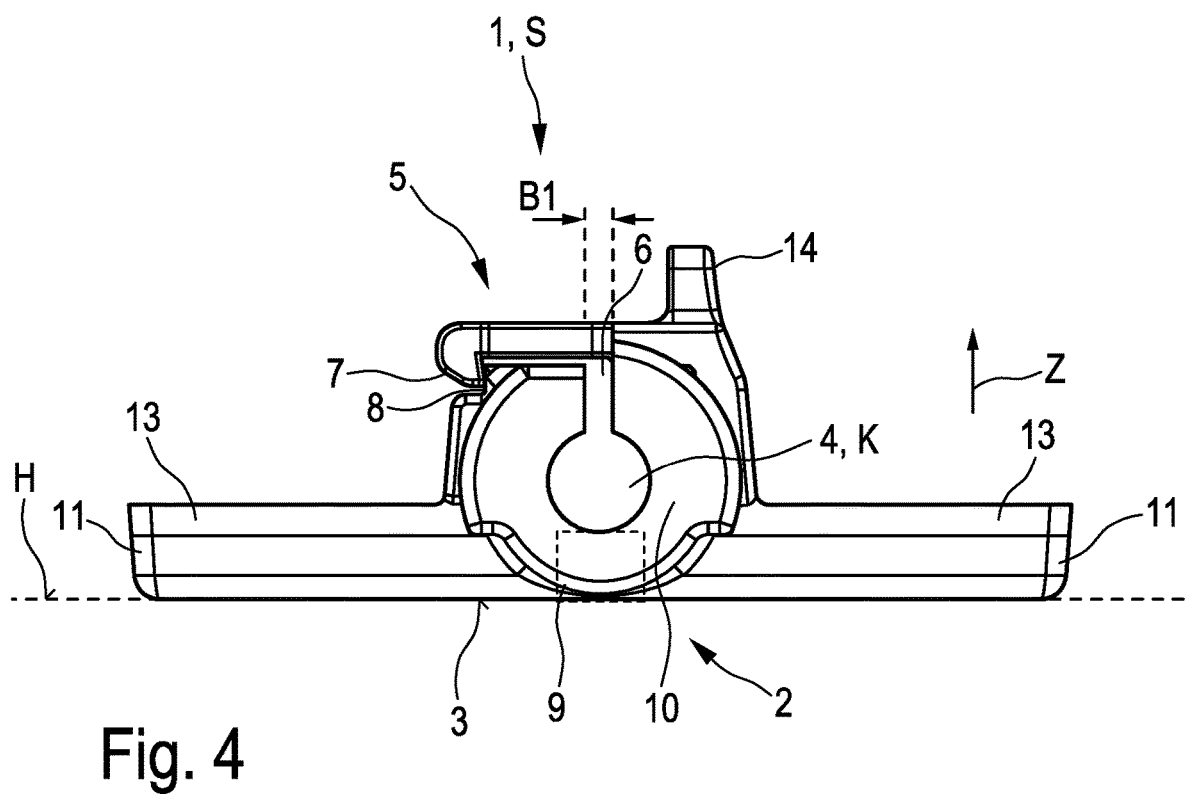
Figure 5:
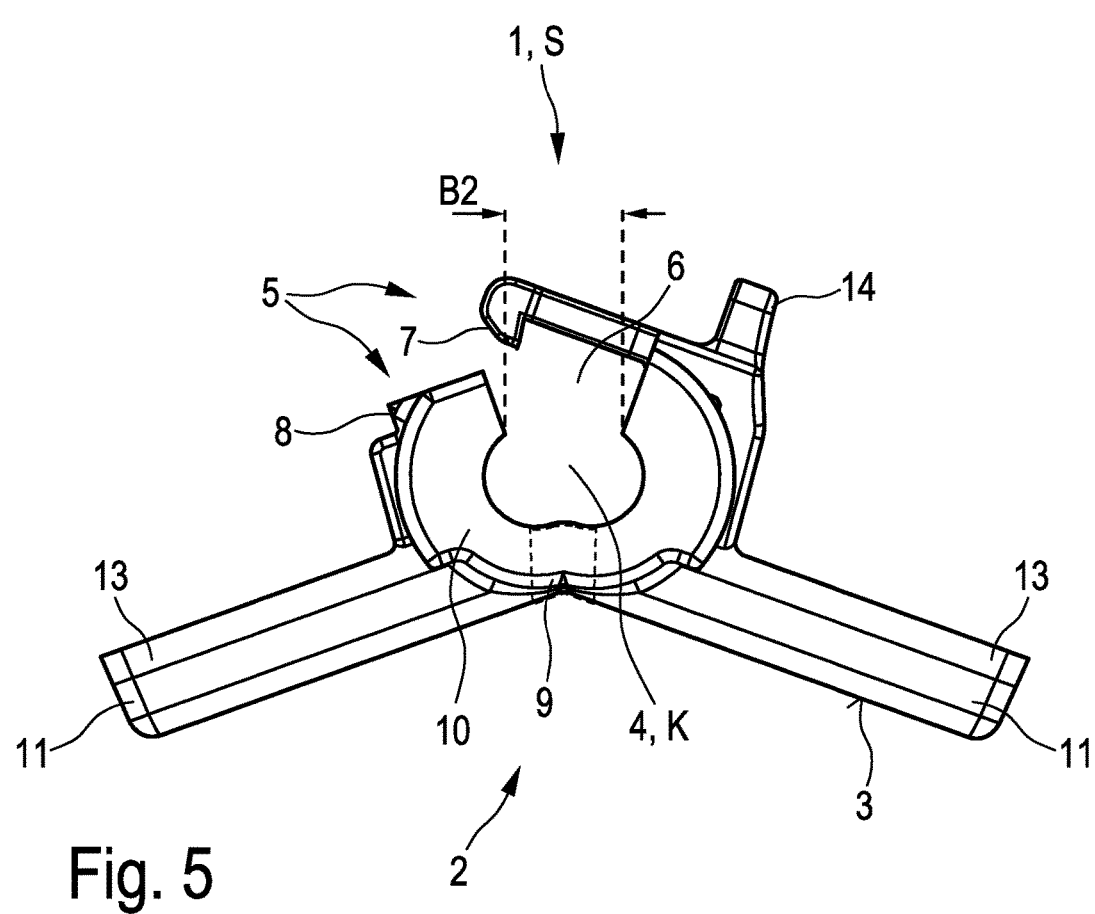

FIG. 1 shows a schematic perspective view of an embodiment of a fixing device according to the invention, in a closed state, FIG. 2 shows a view according to FIG. 1, with the fixing device according to FIG. 1 in an opened state, FIG. 3 shows a perspective cross-sectional view of the fixing device according to FIGS. 1 and 2, in the opened state, and FIGS. 4 and 5 each show a schematic side view, directed axially toward a receiving recess, of the fixing device according to FIGS. 1 to 3 in the closed state (FIG. 4) and in the opened state (FIG. 5).

DETAILED DESCRIPTION

According to FIG. 1, a fixing device 1 is provided for fixing a catheter assembly (not shown in the drawings) to a patient. The catheter assembly to be fixed is in the present case a central venous catheter assembly. Such catheter assemblies are well known and can be designed with a single lumen or with multiple lumens and have at least one hose portion arranged outside of the patient, in the applied state of the catheter assembly. However, the fixing device 1 can also be used for fixing other kinds of catheter assemblies.

The fixing device 1 has a receiving unit 2, which is provided for connection to a skin surface H (FIG. 4) of the patient. The skin surface H is shown in a highly schematic and simplified manner in FIG. 4. It will be seen from the latter that the receiving unit 2, in the configuration shown in FIG. 4, lies with a rear face 3 flat on the skin surface H, wherein the receiving unit 2 is connected to the skin surface H in a manner that will be described in more detail. The receiving unit 2 has a receiving recess 4. The receiving recess 4 is provided to receive a portion of the catheter assembly. In the present case, the receiving recess 4 is provided to receive said hose portion of the catheter assembly. Moreover, the fixing device 1 has a closure unit 5, which serves to close and open the receiving recess 4 at least in a vertical direction Z of the fixing device 1. For this purpose, the closure unit is movable between an opened state (FIGS. 2, 3 and 5), in which the receiving recess 4 is open for receipt and/or removal of the hose portion of the catheter assembly, and a closed state (FIGS. 1 and 4), in which the receiving recess 4 is at least partially closed by means of the closure unit 5.

In the present case, the closure unit 5 is joined non-releasably to the receiving unit 2, wherein the receiving unit 2 is designed at least in part with shape elasticity, such that the closure unit 5 is movable between the opened state and the closed state by means of an elastic deformation of the receiving unit 2.

In order to achieve the at least partial shape elasticity and deformability of the receiving unit 2, the latter in the present case is made of a flexible plastic K1 (FIG. 3). By contrast, the closure unit 5 is made of a substantially dimensionally stable plastic K2. In the present case, a silicone elastomer is chosen as the flexible plastic K1. As will be seen later, particularly in connection with FIG. 3, the receiving unit 2 and the closure unit 5 are made as one continuous piece. The whole fixing device 1 is to this extent designed as an integral structure in the form of a multi-component injection molding S. In the present configuration, the multi-component injection molding S is a two-component injection molding. Methods for producing multi-component moldings or in particular two-component moldings made of plastic are well known in the field of plastics technology.

The receiving recess 4 is designed here in the form of an elongate channel K. The channel K has a longitudinal slit 6 for the introduction of the hose portion into the channel K and/or for the removal of the hose portion from the channel K. The longitudinal slit 6 extends, in the axial direction X of the channel K, along the entire length thereof. A slit width B1, B2 of the longitudinal slit 6 is modifiable by means of the elastic deformation of the receiving unit 2. In the closed state, the longitudinal slit 6 has a slit width B1 and, in the opened state, it has a by comparison larger slit width B2.

The closure unit 5 has a latching portion 7 and a mating latching portion 8. The latching portion is designed in the form of a latching hook 7. The mating latching portion is in the present case designed in the form of a latching projection 8. In the closed state, the latching portion 7 and the mating latching portion 8 are secured on each other with form-fit engagement. By contrast, in the opened state, the latching portion 7 and the mating latching portion 8 are freed from each other. Here, the latching portion 7 and the mating latching portion 8 are pivotable relative to each other about a pivot axis A, wherein the receiving unit 2 has an elastic flexure portion 9 which permits the relative pivotability of the latching portion 7 and of the mating latching portion about the pivot axis A (FIG. 3). The pivot axis A and the longitudinal direction X of the receiving recess 4 and of the channel K are oriented parallel to each other in the present case. The flexure portion 9 is arranged beneath the channel K in the vertical direction Z and permits an elastic bending mobility of the receiving unit 2 and thus a corresponding pivotability of the closure unit 5 for the transfer between the closed state and the opened state. Further functional and structural details of the fixing device 1 are dealt with in more detail below.

The receiving unit 2 has a main portion 10 and, on opposite transverse sides of the main portion 10, two laterally protruding wing portions 11. The main portion 10 has a substantially circular cylindrical basic shape, wherein the channel K extends more or less centrally through the main portion 10 along the longitudinal direction X. At any rate in the closed state (FIGS. 1 and 4), the channel K has a round cross-sectional shape. The two wing portions 11 each have a plate-like, rectangular basic shape and, in relation to the vertical direction Z, are arranged beneath a horizontally oriented central longitudinal plane of the main portion 10. The wing portions 11 each have a through-bore 12. In relation to the longitudinal direction X, the through-bores 12 are arranged more or less centrally on the wing portions 11. The same applies in relation to an arrangement of the through-bores 12 oriented transversely with respect to the longitudinal direction X. The through-bores 12 allow the fixing device 1 to be fastened to the skin surface H by means of medical suture material. This kind of fastening is well known. In an embodiment not shown in detail, the rear face 3 can be prepared for being adhesively affixed to the skin surface H. At the ends, the main portion 10 protrudes beyond the wing portions 11 to both sides in the longitudinal direction X. In the closed state, the wing portions 11 are oriented flat. By contrast, in the opened state, the wing portions 11 are pivoted downward relative to each other about the pivot axis A on account of the elastic bending deformation in the region of the flexure portion 9. Starting from the round cross-sectional shape described above, the channel K is thus widened in the radial direction and folded open at the top, such that the longitudinal slit 6 is widened from the slit width B1 to the slit width B2.

The closure unit 5, to put it simply, is injected molded onto the top of the receiving unit 2 and connected integrally thereto. The closure unit 5 has two side portions 13 that cover the wing portions 11 two-dimensionally. The through-bores 12 extend through the side portions 13. Starting from the wing portions 11, the side portions 13 engage centrally over the main portion 10 on both sides of the channel K, wherein the latching portion 7 is arranged on what is the right-hand side portion 13 in relation to the drawing planes of FIGS. 4 and 5, and the mating latching portion 8 is arranged on the left-hand side portion 13. Moreover, the closure unit 5 has a handling portion 14. The latter is arranged on the right-hand side portion 13 and is designed in the form of a projection protruding in the vertical direction Z. In the closed state, the latching portion 7 engages over the top of the channel K, such that undesired slipping of the hose portion out of the channel K through the longitudinal slit 6 is counteracted. Moreover, the present configuration of the closure unit 5 has the effect that the channel K, in the closed state, is elastically prestressed in the radial direction, such that the hose portion is secured on the channel K with frictional engagement in the axial direction, i.e. in the longitudinal direction X of the channel K. This counteracts undesired slipping of the hose portion along the channel K.

To fix the catheter assembly, the hose portion is introduced into the channel K through the longitudinal slit 6 in the opened state of the closure unit 5. If necessary, the receiving unit 2 can for this purpose be elastically deformed beyond the deformation state shown in FIGS. 2, 3 and 5, such that the hose portion can be easily moved past the latching portion 7 and into the channel K through the longitudinal slit 6. To transfer the closure unit 5 to the closed state (FIGS. 1 and 4), the fixing device 1 is pressed down onto the skin surface H by means of manual pressure in the region of the handling portion 14. This causes a flexurally elastic deformation of the receiving unit 2 in the region of the flexure portion 9, as a result of which the latching portion 7 is pivoted about the pivot axis A relative to the mating latching portion 8, until a form-fit latched connection is produced. The fixing device 1 can be sutured to the skin surface H in the manner described above, although this does not necessarily have to be the case. To remove the hose portion from the channel K, the closure unit 5 can be transferred to the opened state by means of an actuation of the handling portion 14 and/or by means of pressing the side portions 13 down manually. The design of the fixing device 1 according to the invention in principle allows it to be operated with one hand, which makes it considerably easier to manipulate.

The invention claimed is:

1. A fixing device for fixing a catheter assembly to a patient, the fixing device comprising:
a receiving unit having a bottom surface provided for connection to a skin surface of the patient,
a receiving recess, which is arranged on the receiving unit to receive and frictionally engage a portion of the catheter assembly, and
a closure unit comprising a first side portion non-releasably joined to the receiving unit on a first side of the receiving recess, and a second side portion provided separately from the first side portion and non-releasably joined to the receiving unit on a second side of the receiving recess such that the closure unit does not extend between the receiving recess and the bottom surface of the receiving unit, wherein the first side portion and the second side portion are movable relative to the receiving recess between an opened state of the closure unit, in which the receiving recess is open for receipt and/or removal of the portion of the catheter assembly, and a closed state of the closure unit, in which the receiving recess is at least partially closed by the closure unit,
the receiving unit comprising a flexure portion between the receiving recess and the bottom surface of the receiving unit, the flexure portion defining a region about which a first portion of the bottom surface flexes relative to a second portion of the bottom surface when the closure unit is moved between the opened state of the closure unit and the closed state of the closure unit,
the receiving unit being designed with shape elasticity throughout the flexure portion, such that the closure unit is movable between the opened state of the closure unit and the closed state of the closure unit by an elastic deformation of the receiving unit at the flexure portion,
the receiving unit being made of a flexible plastic,
the closure unit being made of a substantially dimensionally stable plastic;
wherein:
the receiving unit is monolithically formed from a first plastic material which is the flexible plastic,
the closure unit is made of a second plastic material which is the substantially dimensionally stable plastic and wherein the second plastic material is different from the first plastic material, and
the first plastic material extends continuously from the receiving recess to the bottom surface of the receiving unit.

2. The fixing device as claimed in claim 1, wherein the receiving unit and the closure unit are made as one continuous piece formed of a multi-component injection molding from at least two different plastics, the at least two different plastics comprising the flexible plastic and the substantially dimensionally stable plastic.

3. The fixing device as claimed in claim 1, wherein the receiving recess comprises a channel that is elongated, the channel having a longitudinal slit for introducing a hose portion of the catheter assembly into the channel, wherein a slit width of the longitudinal slit is modifiable by the elastic deformation of the receiving unit at the flexure portion.

4. The fixing device as claimed in claim 3, wherein the closure unit, in the closed state of the closure unit, causes an at least partial elastic prestressing of the channel in a radial direction of the channel, in order to frictionally fix the hose portion in an axial direction of the channel.

5. The fixing device as claimed in claim 1, wherein the closure unit has a latching portion and a complementary mating latching portion, wherein the latching portion and the complementary mating latching portion are movable relative to each other by the elastic deformation of the receiving unit at the flexure portion.

6. The fixing device as claimed in claim 5, wherein the latching portion and the complementary mating latching portion are pivotable relative to each other about a pivot axis that extends through the flexure portion, the flexure portion permitting relative pivotability of the latching portion and of the complementary mating latching portion.

7. The fixing device as claimed in claim 1, wherein the receiving unit further comprises a first wing portion and a second wing portion, the flexure portion being positioned between the first wing portion and the second wing portion.

8. The fixing device as claimed in claim 7, wherein the receiving unit is deformable at the flexure portion to:
a first state, in which the first wing portion and the second wing portion are parallel, and
a second state, in which the first wing portion and the second wing portion are non-parallel,
the closure unit being moved to the closed state of the closure unit when the receiving unit is deformed to the first state, and
the closure unit being moved to the opened state of the closure unit when the receiving unit is deformed to the second state.

9. The fixing device as claimed in claim 8, wherein the closure unit is disengaged from the closed state of the closure unit to the opened state of the closure unit by pressing downwardly on the first wing portion and the second wing portion.

10. A fixing device for fixing a catheter assembly to a patient, the fixing device comprising:
a receiving unit comprising a top surface, a bottom surface provided for connection to a skin surface of the patient, and a channel for receiving and frictionally engaging a portion of the catheter assembly through the top surface; and
a closure unit comprising:
a first latch attached to the top surface of the receiving unit on a first side of the channel; and
a second latch provided separately from the first latch and attached to the top surface of the receiving unit on a second side of the channel opposite the first side such that the closure unit does not extend between the channel and the bottom surface of the receiving unit,
the receiving unit defining a flexure portion between the channel and the bottom surface,
the flexure portion being bendable between a flexed state and an extended state,
the first latch being detached from the second latch when the flexure portion is in the flexed state to provide access to the channel, and
the first latch being engaged with the second latch when the flexure portion is in the extended state to close the channel,
wherein the flexure portion comprises a region about which a first portion of the bottom surface flexes relative to a second portion of the bottom surface when the flexure portion is moved between the flexed state and the extended state, wherein the receiving unit comprises a first wing portion and a second wing portion, the flexure portion being positioned between the first wing portion and the second wing portion, the receiving unit comprises a main portion having a first wall extending directly upward from a top surface of the first wing portion on a first side of the flexure portion and a second wall extending directly upward from a top surface of the second wing portion on a second side of the flexure portion, wherein the first wall and the second wall define lateral sides of the channel, and wherein the first wing portion, the first wall, the second wing portion, the second wall, and the flexure portion are monolithically formed from a first plastic material;

the first latch extends along the first wing portion and vertically along the first wall opposite the channel;

the second latch extends along the second wing portion and vertically along the second wall opposite the channel; and the first latch and the second latch each comprise a second plastic material that is different from the first plastic material.

11. The fixing device as claimed in claim 10, wherein the flexure portion is bendable about a bending axis, and the channel has a longitudinal direction that is parallel to the bending axis.

12. The fixing device as claimed in claim 10, wherein the channel opens to the top surface of the receiving unit through a slit.

13. The fixing device as claimed in claim 12, wherein the slit and the flexure portion are located on diametrically opposite sides of the channel when the channel is viewed in a cross section.

14. The fixing device as claimed in claim 10, wherein the first wing portion and the second wing portion are parallel to one another when the flexure portion is in the extended state.

15. The fixing device as claimed in claim 10, wherein the first wing portion and the second wing portion are non-parallel to one another when the flexure portion is in the flexed state.

16. The fixing device as claimed in claim 10, wherein the first latch is detachable from the second latch by pressing downwardly on the first wing portion and the second wing portion and bending the flexure portion to the flexed state.

17. A fixing device for fixing a catheter assembly to a patient, the fixing device comprising:
- a main portion having an upper side and a lower side, and the main portion comprising:
  - an outer wall extending along a longitudinal direction,
  - an inner wall monolithically formed with the outer wall extending along the longitudinal direction and defining a receiving recess that is hollow, the receiving recess configured to receive a portion of the catheter assembly, wherein the receiving recess is defined in an entirety of the receiving recess by the inner wall,
  - a flexure portion defined between the outer wall and the inner wall at the lower side of the main portion, the flexure portion extending along a pivot axis, wherein the pivot axis is parallel to the longitudinal direction, and
  - a longitudinal slit extending from the outer wall to the inner wall at the upper side of the main portion, the longitudinal slit extending along an entire length of the receiving recess along the longitudinal direction,
  - wherein the main portion is bendable about the pivot axis between a closed position in which the longitudinal slit has a first opening width as viewed along the longitudinal direction, and an open position in which the longitudinal slit has a second opening width as viewed along the longitudinal direction, wherein the second opening width is larger than the first opening width;
- a first wing portion extending directly from the outer wall of the main portion adjacent to the flexure portion along a first direction, the first wing portion having a lower first wing surface directly joined to the lower side of the main portion, and an upper first wing surface facing opposite the lower first wing surface;
- a second wing portion extending directly from the outer wall of the main portion adjacent to the flexure portion along a second direction, the second wing portion having a lower second wing surface directly joined to the lower side of the main portion, and an upper second wing surface facing opposite the lower second wing surface; and
- a closure unit comprising:
  - a first side portion non-releasably joined to the upper first wing surface,
  - a first upright portion joined to and extending from the first side portion along the outer wall of the main portion and away from the upper first wing surface,
  - a first latching portion located at an end of the first upright portion opposite the first side portion,
  - a second side portion non-releasably joined to the upper second wing surface,
  - a second upright portion joined to and extending from the second side portion along the outer wall of the main portion and away from the upper second wing surface,
  - a second latching portion located at an end of the second upright portion opposite the second side portion, wherein the second latching portion extends over the longitudinal slit and is connectable to the first latching portion when the main portion is in the closed position;
- wherein:
  - the main portion, the first wing portion and the second wing portion are formed from a same flexible plastic material, and
  - the first side portion, the first upright portion, the first latching portion, the second side portion, the second upright portion and the second latching portion are formed from a same substantially dimensionally stable plastic material.

18. The fixing device according to claim 17, wherein the main portion, the first wing portion and the second wing portion are monolithically formed from the same flexible plastic material.

* * * * *